US010274609B2

(12) United States Patent
Robinson et al.

(10) Patent No.: US 10,274,609 B2
(45) Date of Patent: Apr. 30, 2019

(54) SYSTEMS AND METHODS FOR ASSAYING A RADIOACTIVE GAS, AND RELATED SCINTILLATION CELLS

(71) Applicants: BATTELLE ENERGY ALLIANCE, LLC, Idaho Falls, ID (US); Battelle Memorial Institute, Richland, WA (US)

(72) Inventors: Troy A. Robinson, Idaho Falls, ID (US); Martha R. Finck, Idaho Falls, ID (US); Matthew W. Cooper, Richland, WA (US); James C. Hayes, Richland, WA (US); Edward L. Reber, Idaho Falls, ID (US)

(73) Assignees: Battelle Energy Alliance, LLC, Idaho Falls, ID (US); Battelle Memorial Institute, Richland, WA (US)

( * ) Notice: Subject to any disclaimer, the term of this patent is extended or adjusted under 35 U.S.C. 154(b) by 105 days.

(21) Appl. No.: 15/590,359

(22) Filed: May 9, 2017

(65) Prior Publication Data

US 2018/0329077 A1 Nov. 15, 2018

(51) Int. Cl.
*G01T 1/00* (2006.01)
*G01T 1/20* (2006.01)
(Continued)

(52) U.S. Cl.
CPC ........... *G01T 1/003* (2013.01); *G01N 21/766* (2013.01); *G01T 1/1645* (2013.01);
(Continued)

(58) Field of Classification Search
CPC .. G01T 1/003; G01T 7/00; G01T 1/20; G01T 1/1645; G01T 1/1663; G01T 7/02; G21F 9/02; G21F 9/008; G01N 21/766
(Continued)

(56) References Cited

U.S. PATENT DOCUMENTS 4,479,054 A * 10/1984 Kampf .................... G01T 1/204
250/328

OTHER PUBLICATIONS

Cooper et al., "Absolute Efficiency Calibration of a Beta-Gamma Detector", IEEE Transaction of Nuclear Science, vol. 60(2), (Apr. 2013) pp. 676-680.
Cooper et al., "Redesigned β-γ radioxenon detector", Nuclear Instruments and Methods in Physics Research, Section A, vol. 579 (2007) pp. 426-430.
Khandaker, "High purity germanium detector in gamma-ray spectrometry", IJFPS, vol. 1, No. 2 (Jun. 2011) pp. 42-26.
Mcintyre et al., "Concentration independent calibration of β-γ coincidence detector using 131mXe and 133Xe", J Radioanal Nucl Chem, vol. 282, (2009) pp. 755-759.
(Continued)

*Primary Examiner* — David P Porta
*Assistant Examiner* — Gisselle M Gutierrez
(74) *Attorney, Agent, or Firm* — TraskBritt (57) ABSTRACT

A radioactive gas assay system comprises a scintillation cell production assembly, a detector assembly, a computer assembly, and a scintillation cell destruction assembly. The scintillation cell production assembly is configured to produce a scintillation cell comprising a glass scintillator shell containing a volume of radioactive gas. The detector assembly is configured to receive the scintillation cell and to detect photons emitted thereby. The computer assembly is configured to receive data from the detector assembly to automatically calculate an absolute activity of the volume of radioactive gas of the scintillation cell and radiation detection efficiencies of the detector assembly. The scintillation cell destruction assembly is configured to receive the scintillation cell and to rupture the substantially non-porous glass scintillator shell to release the volume of radioactive gas. A method of assaying a radioactive gas, and a scintillation cell are also described.

17 Claims, 3 Drawing Sheets

(51) Int. Cl.
  *G01T 1/166* (2006.01)
  *G01T 1/164* (2006.01)
  *G01T 7/02* (2006.01)
  *G01N 21/76* (2006.01)
  *G21F 9/00* (2006.01)
  *G01T 7/00* (2006.01)
  *G21F 9/02* (2006.01)

(52) U.S. Cl.
  CPC .............. *G01T 1/1663* (2013.01); *G01T 1/20* (2013.01); *G01T 7/00* (2013.01); *G01T 7/02* (2013.01); *G21F 9/008* (2013.01); *G21F 9/02* (2013.01)

(58) Field of Classification Search
  USPC ........................................................ 250/380
  See application file for complete search history.

(56) References Cited

OTHER PUBLICATIONS

Mcintyre et al., "Further developments of a robust absolute calibration method utilizing beta/gamma coincidence techniques", J Radioanal Nucl Chem, vol. 296, (Sep. 2012) pp. 693-698.

Mcintyre et al., "Measurements of ambient radioxenon levels using the automated radioxenon sampler/analyzer (ARSA)", Journal of Radioanalytical and Nuclear Chemistry, vol. 248, No. 3, (2001) pp. 629-635.

Reeder et al., "Beta-gamma counting system for Xe fission products", Journal of Radioanalytical and Nuclear Chemistry, vol. 235, Nos. 1-2, (1998) pp. 89-94.

Reeder et al., "Delayed coincidence technique for 133gXe detection", Nuclear Instruments and Methods in Physics Research, Section A, vol. 408, (1998) pp. 573-581.

* cited by examiner

SYSTEMS AND METHODS FOR ASSAYING A RADIOACTIVE GAS, AND RELATED SCINTILLATION CELLS

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The disclosure, in various embodiments, relates generally to systems, methods, devices, and structures for assaying a radioactive gas.

BACKGROUND

As a result of the Comprehensive Test Ban Treaty (CTBT), monitoring stations have been established by the Comprehensive Test Ban Treaty Organization (CTBTO) as part of an International Monitoring System (IMS) that incorporates seismic, acoustic, and radionuclide monitoring processes to detect nuclear detonations. Some such monitoring stations are configured to continuously monitor air for the detection of fission product radioactive isotopes of xenon (Xe) (also referred to as "radioxenon"). The detection of radioxenon in the air definitively confirms that nuclear fission has occurred. To ensure the accuracy of the systems (e.g., beta-gamma coincidence counting systems) employed at the monitoring stations to detect radioxenon, the detectors used by the systems are regularly calibrated for detection efficiency.

Some methods of detector efficiency calibration utilize a calibration standard separate from a gas sample to be assayed. However, such efficiency calibrations are only valid where the calibration standard has substantially the same geometric configuration and substantially the same activity as the gas sample to be assayed. It can be difficult to procure a calibration standard in the exact geometric configuration used for a gas sample to be assayed, and transferring a calibration standard to the geometric configuration of the gas sample usually voids the certified value of the standard. In addition, a calibration standard can suffer from uncertainties in its certified value propagated from the sum total of the uncertainties in the various measurements made during the production of the calibration standard, as well as uncertainties associated with the fitting (e.g., polynomial fitting) observed activities of the calibration standard (e.g., if the calibration standard includes multiple radioactive isotopes).

Other methods of detector efficiency calibration involve absolute efficiency calibration (AEC) through coincidence counting to determine absolute activity and absolute detection efficiency through the comparison of coincidence and anti-coincidence events with the known decay branching ratio data. Such calibration methods can be effectuated without the use of a calibration standard separate from a gas sample being assayed by the system. A quantified gas sample including a radioxenon isotope (e.g., xenon-133) is typically directed into an opening (e.g., a well) in a detector (e.g., a gamma ray well detector) lined (e.g., coated) with a porous solid organic scintillator, and is then subjected to AEC analysis to determine the absolute activity of the quantified gas sample and the absolute detection efficiency of the detector. Unfortunately, a portion of the quantified gas sample can become irremovably trapped within the pores of the porous solid organic scintillator, resulting in the destruction of the quantified gas sample, as well as detector memory effects effectuated by the trapped portion of the quantified gas sample. The memory effects can usually be corrected for to allow the detector to be used for subsequent gas sample assay, but such corrections can undesirably require implementing increased radioxenon detection limits.

It would, therefore, be desirable to have new systems, methods, devices, and structures for assaying a radioactive gas (e.g., to determine the absolute activity of the radioactive gas, and detection efficiencies of employed radiation detector(s)), such as gas including one or more radioxenon isotopes, that are more efficient, more accurate, and/or more versatile as compared to conventional systems, conventional methods, conventional devices, and conventional structures.

BRIEF SUMMARY

Embodiments described herein include systems, methods, devices, and structures for assaying a radioactive gas. In accordance with one embodiment described herein, a radioactive gas assay system comprises a scintillation cell production assembly, a detector assembly, a computer assembly, and a scintillation cell destruction assembly. The scintillation cell production assembly is configured to produce a scintillation cell comprising a glass scintillator shell containing a volume of radioactive gas. The detector assembly is configured to receive the scintillation cell and to detect photons emitted by the scintillation cell. The computer assembly is operatively associated with and configured to receive data from the detector assembly to automatically calculate an absolute activity of the volume of radioactive gas of the scintillation cell as well as radiation detection efficiencies of the detector assembly. The scintillation cell destruction assembly is configured to receive the scintillation cell and to rupture the substantially non-porous glass scintillator shell thereof to release the volume of radioactive gas contained therein.

In additional embodiments, a method of assaying a radioactive gas comprises forming a scintillation cell comprising a substantially non-porous glass scintillator shell containing a volume of radioactive gas. The scintillation cell is delivered into a detector assembly comprising a gamma well detector and a light sensor to detect photons emitted from the scintillation cell. An absolute activity of the volume of radioactive gas of the scintillation cell and radiation detection efficiencies of the detector assembly are calculated using a computer assembly in communication with the detector assembly. The scintillation cell is then removed from the detector assembly.

In further embodiments, a scintillation cell comprises a volume of radioactive gas, and a glass scintillator shell completely encapsulating the volume of radioactive gas. The volume of radioactive gas comprises one or more of $^{127}$Xe, $^{131m}$Xe, $^{133}$Xe, $^{133m}$Xe, and $^{135}$Xe. The glass scintillator shell comprises a glass scintillator material substantially impermeable to the volume of radioactive gas.

DETAILED DESCRIPTION

Systems, methods, devices, and structures for assaying a radioactive gas are described. In some embodiments, a radioactive gas assay system includes a scintillation cell production assembly, a detector assembly, a computer assembly, and a scintillation cell destruction assembly. The scintillation cell production assembly is configured to produce a scintillation cell including a glass scintillator shell, and a volume of radioactive gas (e.g., a volume of gas including one or more radioxenon isotopes) contained within the glass scintillator shell. The glass scintillator shell may be substantially non-porous, such that the glass scintillator shell is substantially impermeable to the volume of radioactive gas. Radioactive isotopes of the radioactive gas are not absorbed by and do no diffuse through glass scintillator shell. The detector assembly is configured to receive the scintillation cell produced by the scintillation cell production assembly, and to detect photons (e.g., gamma photons, scintillation photons) emitted from the scintillation cell. The computer assembly is operatively associated with the detector assembly, and is configured to receive data (e.g., photon counting data) from the detector assembly to automatically calculate an absolute activity of the volume of radioactive gas of the scintillation cell, as well as radiation detection efficiencies (e.g., beta detection efficiency and gamma detection efficiency) of the detector assembly. The scintillation cell destruction assembly is configured to receive the scintillation cell (e.g., following the analysis thereof using the detector assembly and the computer assembly) to rupture (e.g., crush, crack, break) the glass scintillator shell thereof and release the volume of radioactive gas contained therein. The released volume of radioactive gas may be recovered, and subsequently utilized as desired. The systems, methods, devices, and structures of the disclosure may be more versatile, more accurate, and/or more efficient as compared to conventional systems, conventional methods, conventional devices, and conventional structures for assaying a radioactive gas. In addition, the systems, methods, devices, and structures of the disclosure may also reduce costs (e.g., material costs, such as radioactive gas procurement and/or production costs; radioactive gas disposal costs), risks (e.g., radioactive gas disposal risks), and/or environmental impacts as compared to conventional systems, conventional methods, conventional devices, and conventional structures for assaying a radioactive gas.

In the following detailed description, reference is made to the accompanying drawings that form a part hereof and, in which is shown by way of illustration, specific embodiments in which the disclosure may be practiced. These embodiments are described in sufficient detail to enable those of ordinary skill in the art to practice that described in this disclosure, and it is to be understood that other embodiments may be utilized, and that structural, logical, and electrical changes may be made within the scope of the disclosure.

Referring in general to the following description and accompanying drawings, various embodiments of the disclosure are illustrated to show its structure and method of operation. Common elements of the illustrated embodiments are designated with like reference numerals. It should be understood that the figures presented are not meant to be illustrative of actual views of any particular portion of the actual structure, system, or method, but are merely idealized representations employed to more clearly and fully depict the disclosure defined by the claims below.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of embodiments of the disclosure and such term is used in preference to the more restrictive term "is" so as to avoid any implication that other, compatible materials, structures, features and methods usable in combination therewith should, or must be, excluded.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, if materials in the figures are inverted, elements described as "below" or "beneath" or "under" or "on bottom of" other elements or features would then be oriented "above" or "on top of" the other elements or features. Thus, the term "below" can encompass both an orientation of above and below, depending on the context in which the term is used, which will be evident to one of ordinary skill in the art. The materials may be otherwise oriented (e.g., rotated 90 degrees, inverted, flipped) and the spatially relative descriptors used herein interpreted accordingly.

As used herein, the singular forms "a," "an," and "the" are intended to include the plural forms as well, unless the context clearly indicates otherwise.

As used herein, "and/or" includes any and all combinations of one or more of the associated listed items.

As used herein, the term "configured" refers to a size, shape, material composition, material distribution, and arrangement of one or more of at least one structure and at least one apparatus facilitating operation of one or more of the structure and the apparatus in a predetermined way.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, at least 99.9% met, or even 100.0% met.

As used herein, the term "about" in reference to a given parameter is inclusive of the stated value and has the meaning dictated by the context (e.g., it includes the degree of error associated with measurement of the given parameter).

Figure 1:
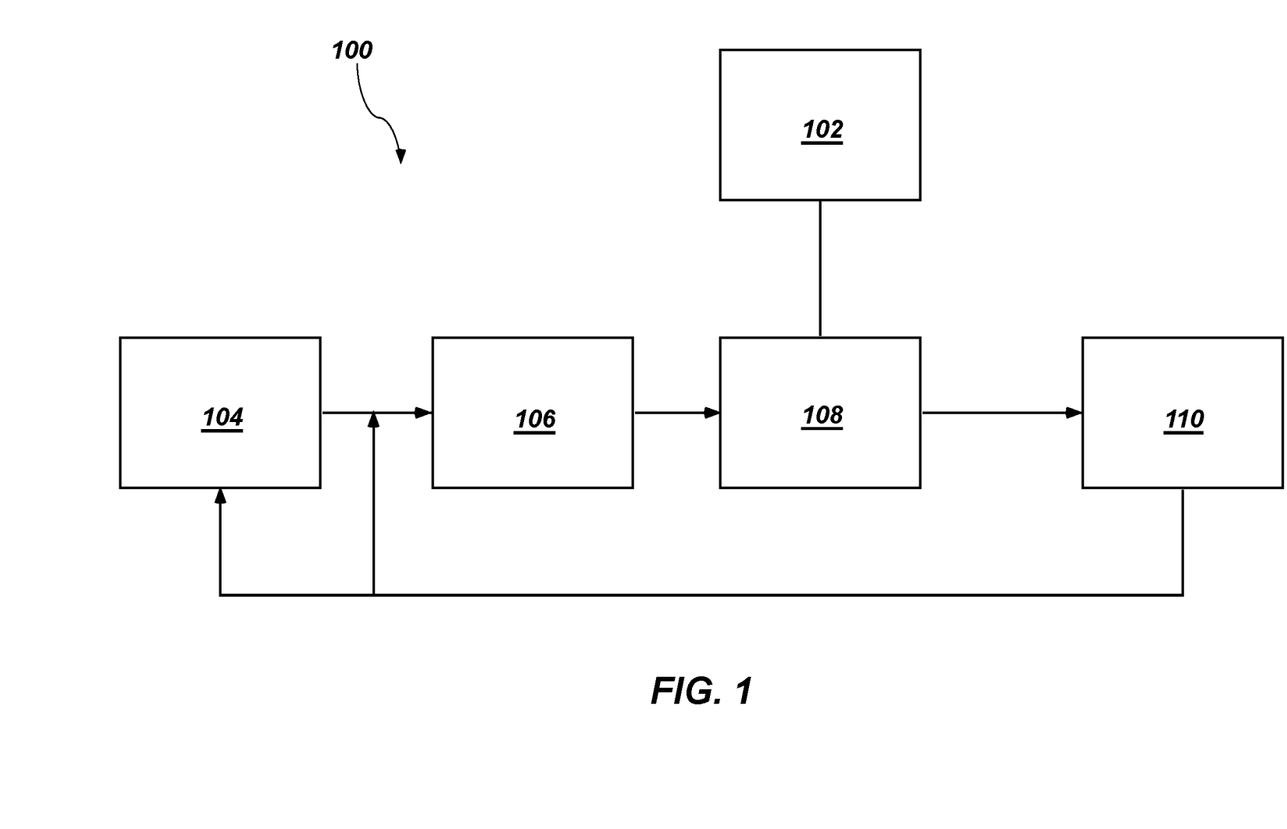
FIG. 1 is a simplified top-down view of a radioactive gas assay system, in accordance with an embodiment of the disclosure.

One embodiment of the disclosure will now be described with reference to FIG. 1, which schematically illustrates a radioactive gas assay system 100. As shown in FIG. 1, the radioactive gas assay system 100 may include a main computer/electronics assembly 102, a radioactive gas source 104, a scintillation cell production assembly 106, a detector assembly 108, and a scintillation cell destruction assembly 110. With the description provided below, it will be readily apparent to one of ordinary skill in the art that the systems and methods described herein may be used in various systems. In other words, the methods and systems of the disclosure may be used whenever it is desired to quantify the radioactivity of a gas.

The main computer/electronics assembly 102 may serve as a common interface facilitating the simple and efficient control and analysis of one or more components (e.g., the detector assembly 108, the scintillation cell production assembly 106, the scintillation cell destruction assembly 110, etc.) of the radioactive gas assay system 100. The main computer/electronics assembly 102 may include devices (e.g., multichannel analyzers, single channel analyzers, analog-to-digital converters, pulse counters, amplifiers, etc.) for receiving and analyzing data from the different components of the radioactive gas assay system 100. In addition, the main computer/electronics assembly 102 may include input devices (e.g., mouse, keyboard, etc.) through which an operator may input information, operate the main computer/electronics assembly 102, and/or electronically operate other operations of the various components of the radioactive gas assay system 100. Furthermore, the main computer/electronics assembly 102 may include output devices or other peripheral devices (e.g., monitors, printers, speakers, etc.) from which an operator may interpret results of measurements, characterization of the measurements, the operational status of the various components of the radioactive gas assay system 100, or other similar information. The main computer/electronics assembly 102 may also include storage media such as hard drives, external hard drives, Flash memory, RAM, ROM, DVDs, and other computer-readable media for storing information related to measurements or status of the various components of the radioactive gas assay system 100.

Computer-readable media, such as storage media, may also be used for executing instructions and operations related to performing, analyzing, characterizing measurements, and/or for controlling various components of the radioactive gas assay system 100. In other words, the main computer/electronics assembly 102 includes control logic, which may include instructions that permit the radioactive gas assay system 100 to operate. The main computer/electronics assembly 102 may utilize control logic to automatically monitor and automatically control (e.g., activate, deactivate, move, position, etc.) various components of the radioactive gas assay system 100. As described in further detail below, the control logic may automatically calculate, at least partially based on measurement data (e.g., gamma photon counts, scintillation photon counts) received from the detector assembly 108, the absolute activity of a volume of radioactive gas contained within a scintillation cell formed in the scintillation cell production assembly 106 prior to further action with respect to the scintillation cell and/or the volume of radioactive gas contained therein. In addition, the control logic may also automatically calculate, at least partially based on the measurement data received from the detector assembly 108, radiation detection efficiencies (e.g., a beta detection efficiency, a gamma detection efficiency) of the detector assembly 108. The control logic may also include a user interface, which may provide operators with prompts and directions for simplified operation for inexperienced operators.

With continued reference to FIG. 1, the radioactive gas source 104 may comprise any device (e.g., apparatus) configured and operated to store (e.g., contain, hold) at least one radioactive gas, and to transfer (e.g., convey, deliver, flow, etc.) the radioactive gas under pressure to the scintillation cell production assembly 106. The radioactive gas source 104 may be in fluid communication with the scintillation cell production assembly 106, and may, optionally, be in electronic communication with the main computer/electronics assembly 102. By way of non-limiting example, the radioactive gas source 104 may comprise a storage vessel (e.g., a pressurized storage tank) configured and operated to contain a radioactive gas and to transfer the radioactive gas to the scintillation cell production assembly 106. Suitable configurations for the radioactive gas source 104 are well known in the art, and therefore are not described in detail herein.

The radioactive gas may be formed of and include one or more radioactive noble gases. For example, the radioactive gas may comprise one or more radioxenon isotopes, such as one or more of xenon-127 ($^{127}$Xe), metastable xenon-131 ($^{131m}$Xe), xenon-133 ($^{133}$Xe), metastable xenon-133 ($^{133m}$Xe), and xenon-135 ($^{135}$Xe). In some embodiments, the radioactive gas includes a single (e.g., only one) radioxenon isotope (e.g., only one of $^{127}$Xe, $^{131m}$Xe, $^{133}$Xe, $^{133m}$Xe, and $^{135}$Xe). In additional embodiments, the radioactive gas includes multiple (e.g., more than one) radioxenon isotopes (e.g., more than one of $^{127}$Xe, $^{131m}$Xe, $^{133}$Xe, $^{133m}$Xe, and $^{135}$Xe). The material composition of the radioactive gas may at least partially depend on the method of producing the radioactive gas, and a desired use of the radioactive gas. For example, the radioactive gas may be formed to include amounts of one or more radioxenon isotopes facilitating the use of a subsequently formed scintillation cell including the radioactive gas to calibrate one or more detectors configured and operated to monitor air for radioxenon.

Figure 2:
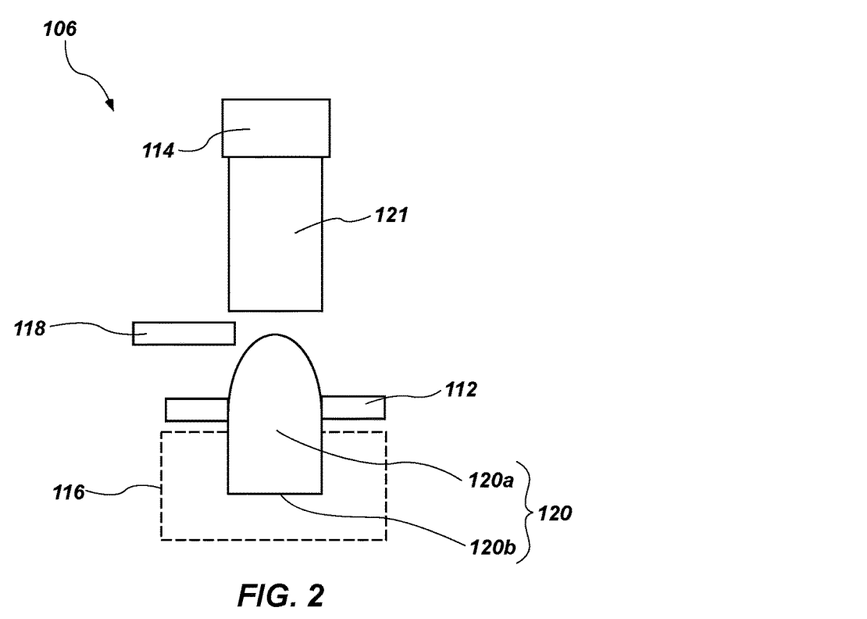
FIG. 2 is a simplified, cross-sectional view of a scintillation cell production assembly of the radioactive gas assay system shown in FIG. 1, in accordance with an embodiment of the disclosure.

The scintillation cell production assembly 106 may be positioned downstream of the radioactive gas source 104, and may be configured and operated to produce a scintillation cell including a volume of radioactive gas from the radioactive gas source 104 and glass scintillator shell (e.g., a glass scintillator bean, a glass scintillator ampule, etc.) completely encapsulating and containing the volume of radioactive gas. FIG. 2 is a simplified, cross-sectional view of the scintillation cell production assembly 106, in accordance with an embodiment of the disclosure. As shown in FIG. 2, the scintillation cell production assembly 106 may include a retention device 112, a radioactive gas delivery device 114, an optional cooling device 116 (as shown by dashed lines), and a sealing device 118.

The retention device 112 of the scintillation cell production assembly 106 is configured and operated to temporarily receive and hold a preliminary glass scintillator structure (e.g., a preliminary glass scintillation vial, a preliminary glass scintillator tube, etc.) to be acted upon (e.g., filled with pressurized radioactive gas and sealed) to form a scintillation cell, as described in further detail below. The retention device 112 may exhibit any components, component shapes, component dimensions, and component arrangements compatible with a configuration (e.g., size, shape, material composition, etc.) of the preliminary glass scintillator structure and with a desired and predetermined configuration of the scintillation cell to be formed from the preliminary glass scintillator structure. In turn, the desired and predetermined configuration of a scintillation cell may be selected at least partially based on a configuration of a detector assembly to receive and temporarily hold the scintillation cell, as also described in further detail below. In some embodiments, the retention device 112 comprises a device (e.g., a tweezer device, a clamp device, etc.) including at least two structures configured and operated to press against opposing regions of the preliminary glass scintillator structure to hold the preliminary glass scintillator structure during the formation of the scintillation cell.

The radioactive gas delivery device 114 of the scintillation cell production assembly 106 is configured and operated to deliver pressurized radioactive gas from the radioactive gas source 104 (FIG. 1) into the preliminary glass scintillator structure. The radioactive gas delivery device 114 may, for example, comprise a tubing structure in fluid communication with each of the radioactive gas source 104 and the preliminary glass scintillator structure. The radioactive gas delivery device 114 may be configured to be temporarily affixed (e.g., temporarily attached) to an inlet of the preliminary glass scintillator structure. The radioactive gas delivery device 114 may exhibit any components, component shapes, component dimensions, and component arrangements compatible with the configurations of the preliminary glass scintillator structure and the radioactive gas source 104.

The cooling device 116 (if present) of the scintillation cell production assembly 106 may comprise at least one device configured and operated to cool the preliminary glass scintillator structure as a portion of the preliminary glass scintillator structure filled with pressurized radioactive gas from the radioactive gas source 104 (FIG. 1) is acted upon by the sealing device 118 to form a scintillation cell, as described in further detail below. By way of non-limiting example, the cooling device 116 may comprise a cryogenic cooling device (e.g., a liquid nitrogen cooling device) configured to receive, partially surround, and cool the portion of the filled preliminary glass scintillator structure to be formed into the scintillation cell.

The sealing device 118 of the scintillation cell production assembly 106 is configured and operated to seal (e.g., flame seal) and separate a portion of the preliminary glass scintillator structure after pressurized radioactive gas from the radioactive gas source 104 (FIG. 1) has been delivered into the preliminary glass scintillator structure to form a scintillation cell 120 and a remaining portion 121 of the filled preliminary glass scintillator structure. By way of non-limiting example, the sealing device 118 may comprise a flame-sealing device (e.g., a torch device) configured and operated to melt (e.g., by way of exposure to flame) and join together opposing portions of one or more sidewalls of the filled preliminary glass scintillator structure. As shown in FIG. 2, the resulting scintillation cell 120 includes a selected volume of radioactive gas 120a at a selected pressure, and a glass scintillator shell 120b completely surrounding (e.g., completely encapsulating) the volume of radioactive gas 120a.

The glass scintillator shell 120b of the scintillation cell 120 formed using the scintillation cell production assembly 106 is configured (e.g., materially composed, sized, shaped, etc.) to substantially contain the selected volume of radioactive gas 120a. The glass scintillator shell 120b may also be configured to maximize gamma radiation (e.g., gamma ray photon) transmissivity through the glass scintillator shell 120b (e.g., minimize gamma radiation attenuation in the glass scintillator shell 120b), and to minimize beta radiation (e.g., beta particle, such as electron) transmissivity through the glass scintillator shell 120b (e.g., maximizing beta radiation absorption and associated scintillation photon generation in the glass scintillator shell 120b).

The glass scintillator shell 120b of the scintillation cell 120 (and, hence, the preliminary glass scintillator structure utilized to form the glass scintillator shell 120b) is formed of and includes a glass scintillator material that generates photons when excited by beta radiation emitted by the volume of radioactive gas 120a. The glass scintillator material may be substantially non-porous, such that the glass scintillator shell 120b is substantially impermeable to the volume of radioactive gas 120a. For example, the glass scintillator material may be formulated such that radioxenon isotopes (e.g., $^{127}$Xe, $^{131m}$Xe, $^{133}$Xe, $^{133m}$Xe, $^{135}$Xe) of the volume of radioactive gas 120a are not substantially absorbed by the glass scintillator shell 120b and do not substantially diffuse (e.g., migrate, permeate) through the glass scintillator shell 120b. As a non-limiting example, the glass scintillator material may comprise a cerium activated lithium silicate glass scintillator having a density within a range of from about 2.40 grams per cubic centimeter (g/cm$^3$) to about 2.65 g/cm$^3$ (e.g., from about 2.42 g/cm$^3$ to about 2.64 g/cm$^3$, or from about from about 2.42 g/cm$^3$ to about 2.50 g/cm$^3$). In some embodiments, the glass scintillator shell 120b is formed of and includes a cerium activated lithium silicate glass scintillator comprising 6.6 weight percent (wt %) lithium (Li), 3.4 wt % cerium (Ce), 27.2 wt % silicon (Si), 50.7 wt % oxygen (O), 9.8 wt % aluminum (Al), and 2.3 wt % magnesium (Mg). In additional embodiments, the glass scintillator shell 120b is formed of and includes a cerium activated lithium silicate glass scintillator comprising 7.5 wt % Li, 4.35 wt % Ce, 36.2 wt % Si, and 51.95 wt % O. The preliminary glass scintillator structure employed to form the glass scintillator shell 120b may be formed from components of the glass scintillator material through conventional processes (e.g., conventional glass blowing processes) and conventional processing equipment, which are not described in detail herein.

Optionally, one or more surfaces (e.g., internal surfaces, external surfaces) of the glass scintillator shell 120b of the scintillation cell 120 may be at least partially coated by an additional scintillator material, such as an organic scintillator material. If present, the organic scintillator material may generate additional photons when excited by beta radiation emitted by the volume of radioactive gas 120a. For example, one or more of internal surfaces and external surfaces of the preliminary glass scintillator structure may be coated with at least one organic scintillator material, and then the resulting coated preliminary glass scintillator structure may then be acted upon to form the scintillation cell 120 using the scintillation cell production assembly 106. As another example, an external surface of the glass scintillator shell 120b may be coated with at least one organic scintillator material following formation of the glass scintillator shell 120b using the scintillation cell production assembly 106. In some embodiments, the surfaces of the glass scintillator shell 120b are substantially free of additional scintillator materials thereon or thereover.

The glass scintillator shell 120b of the scintillation cell 120 may exhibit any shape and any dimensions (e.g., lateral dimensions, longitudinal dimensions, thickness, etc.) compatible with (e.g., complementary to) the shapes and the dimensions of other components (e.g., the detector assembly 108, the scintillation cell destruction assembly 110) of the radioactive gas assay system 100, and facilitating desired analysis (e.g., assay) of the volume of radioactive gas 120a of the scintillation cell 120 using one or more of the other components of the radioactive gas assay system 100. The glass scintillator shell 120b may, for example, exhibit a shape and dimensions permitting the scintillation cell 120 to be received by the detector assembly 108, and to be analyzed using the detector assembly 108 and the main computer/electronics assembly 102, as described in further detail below.

As shown in FIG. 2, in some embodiments, the glass scintillator shell 120*b* of the scintillation cell 120 exhibits a hollow, elongate three-dimensional (3D) shape including a generally tubular body and closed ends, wherein at least one (e.g., only one) of the ends is tapered (e.g., conical). The tapered end of the glass scintillator shell 120*b* may be formed by the sealing device 118 of the scintillation cell production assembly 106 during the formation of the scintillation cell 120. In further embodiments, the glass scintillator shell 120*b* may exhibit a different hollow 3D shape (e.g., a hollow tubular shape with closed, non-tapered ends; a hollow spherical shape; a hollow cubic shape; a hollow cuboidal shape; a hollow conical shape; etc.).

The glass scintillator shell 120*b* of the scintillation cell 120 may exhibit lateral dimensions (e.g., a width, a diameter) and longitudinal dimensions (e.g., a height) permitting the scintillation cell 120 to be substantially completely received within an opening (e.g., a well of a gamma ray well detector) of the detector assembly 108, as described in further detail below. Accordingly, the lateral dimensions of the glass scintillator shell 120*b* are less than the lateral dimensions of the opening of the detector assembly 108, and the longitudinal dimensions of the glass scintillator shell 120*b* are less than or equal to the longitudinal dimensions (e.g., height, depth) of the opening of the detector assembly 108. In some embodiments, the glass scintillator shell 120*b* is sized to permit the scintillation cell 120 to be substantially completely received within an opening having a diameter of about 15.5 millimeters (mm), and a height (e.g., depth) of about 49.2 mm. By way of non-limiting example, the glass scintillator shell 120*b* may exhibit a maximum diameter of less than 15.5 mm (e.g., about 15 mm), and a maximum height less than 49.2 mm (e.g., about 40 mm). In addition, a thickness of the glass scintillator shell 120*b* may be selected relative to a material composition thereof to minimize (e.g., substantially eliminate) beta particle (e.g., electron) transmission through the glass scintillator shell 120*b*, while permitting substantially all photons (e.g., gamma photons, scintillation photons) to escape the glass scintillator shell 120*b*. Minimizing beta particle transmission through (and, hence, enhancing photon generation within) the glass scintillator shell 120*b* and maximizing photon transmission through the glass scintillator shell 120*b* may enhance the accuracy of analytics subsequently performed on the volume of radioactive gas 120*a* of the scintillation cell 120. In some embodiments, the glass scintillator shell 120*b* exhibits a thickness greater than or equal to about 0.2 cm. The thickness of the glass scintillator shell 120*b* may be substantially uniform (e.g., non-variable), or may be at least partially non-uniform (e.g., variable).

While FIG. 2 depicts a particular configuration of the scintillation cell production assembly 106, the scintillation cell production assembly 106 may exhibit a different configuration, such as a configuration exhibiting one or more of different dimensions, a different shape, different features, different feature spacing, different components, and a different arrangement of components. FIG. 2 illustrates just one non-limiting example of the scintillation cell production assembly 106. The scintillation cell production assembly 106 may, for example, include a different configuration of one or more of the retention device 112, the radioactive gas delivery device 114, the optional cooling device 116, and the sealing device 118, and/or a different arrangement of the retention device 112, the radioactive gas delivery device 114, the optional cooling device 116, and the sealing device 118.

Figure 3:
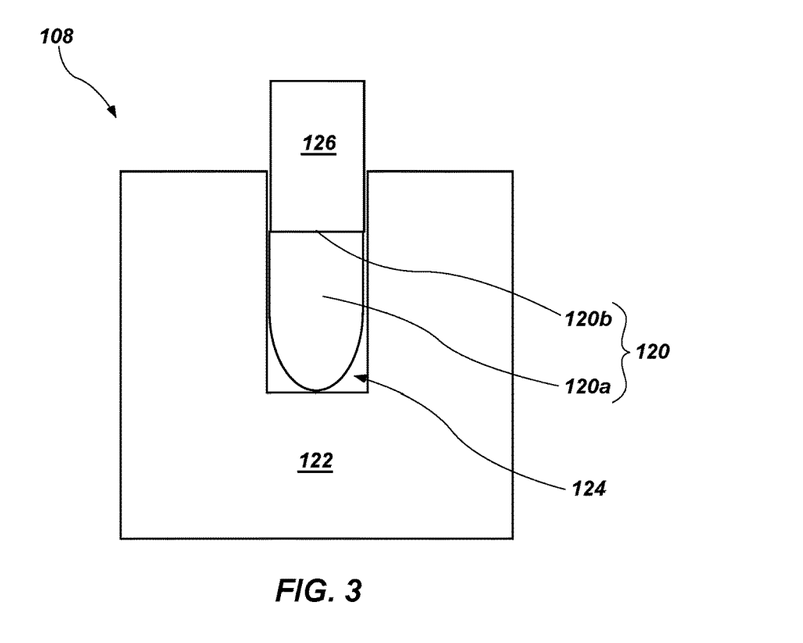
FIG. 3 is a simplified, cross-sectional view of a detection assembly of the radioactive gas assay system shown in FIG. 1, in accordance with an embodiment of the disclosure.

FIG. 3 is a simplified, cross-sectional view of the detector assembly 108, in accordance with an embodiment of the disclosure. As shown in FIG. 3, the detector assembly 108 may include a gamma ray well detector 122 exhibiting a well 124 (e.g., opening, orifice, bore, trench) therein, and a light sensor 126 operatively associated with the gamma ray well detector 122. As described in further detail below, the detector assembly 108 is configured to receive the scintillation cell 120 formed using the scintillation cell production assembly 106, to detect photons (e.g., gamma photons, scintillation photons) emitted by the scintillation cell 120, and to transmit data to the main computer/electronics assembly 102 (FIG. 1) to quantify one or more radioactive isotopes (e.g., one or more radioactive noble gas isotopes, such as one or more radioxenon isotopes) within the volume of radioactive gas 120*a* of the scintillation cell 120 through one or more computer-numerically-assisted processes employing conventional data analysis methodologies (e.g., 4-pi beta-gamma coincidence counting methodologies) for assaying a radioactive gas to determine the absolute activity of the volume of radioactive gas 120*a* as well as the radiation detection efficiencies of the detector assembly 108.

The gamma ray well detector 122 of the detector assembly 108 is configured and operated to receive and hold the scintillation cell 120 within the well 124 therein, and to detect gamma photons emitted by the scintillation cell 120. The gamma ray well detector 122 is separate (e.g., discrete) and distinct from the scintillation cell 120, such that the scintillation cell 120 may be readily provided into and removed from the well 124 of the gamma ray well detector 122. One or more surfaces of the scintillation cell 120 may physically contact one or more surfaces of the gamma ray well detector 122 within the well 124, but the surfaces of the scintillation cell 120 may remain unattached (e.g., uncoupled, unbonded) to the surfaces of the gamma ray well detector 122 within the well 124. In some embodiments, the gamma ray well detector 122 comprises a high-purity germanium (HPGe) well detector. The gamma ray well detector 122 may relay (e.g., transmit, output) gamma photon counting data to the main computer/electronics assembly 102 (FIG. 1).

With continued reference to FIG. 3, the light sensor 126 is configured and operated to detect scintillation photons emitted by the scintillation cell 120. The scintillation photons emitted by the scintillation cell 120 may be generated by the glass scintillator shell 120*b* of the scintillation cell 120 when the glass scintillator material of the glass scintillator shell 120*b* is excited by beta radiation (e.g., beta particles) emitted by the volume of radioactive gas 120*a* of the scintillation cell 120. As shown in FIG. 3, the light sensor 126 may be provided on or over the scintillation cell 120 within the well 124 of the gamma ray well detector 122. The light sensor 126 may be configured and positioned to at least partially extend into the well 124 of the gamma ray well detector 122. In addition, the light sensor 126 may be separate and distinct from the scintillation cell 120 and the gamma ray well detector 122. In some embodiments, the light sensor 126 comprises a photomultiplier tube (PMT). The light sensor 126 may relay (e.g., transmit, output) scintillation photon counting data to the main computer/electronics assembly 102 (FIG. 1).

The main computer/electronics assembly 102 (FIG. 1) may utilize the gamma photon counting data received from the gamma ray well detector 122 and the scintillation photon counting data received from the light sensor 126 to automatically calculate the absolute activity of the volume of radioactive gas 120a and radiation detection efficiencies (e.g., a beta detection efficiency, and a gamma detection efficiency) of the detector assembly 108 based on determined coincidence (e.g., beta-gamma coincidence) and anti-coincidence (e.g., single beta, and single gamma) event counts, emission probabilities, and detector interaction probabilities through conventional data analysis methodologies, such as those described in M. Cooper, et. al., *Absolute Efficiency Calibration of a Beta-Gamma Detector*, IEEE Transactions of Nuclear Science, 60(2): 676-680 (April 2013), the entire disclosure of which is incorporated in its entirety herein by reference. The process facilitates the automatic calibration (e.g., automatic absolute efficiency calibration) of the detector assembly 108 as the detector assembly 108 counts the photons emitted by scintillation cell 120, forgoing (e.g., negating) a need for a secondary calibration source (e.g., a calibration standard separate from the scintillation cell 120) to calibrate the detector assembly 108.

While FIG. 3 depicts a particular configuration of the detector assembly 108, the detector assembly 108 may exhibit a different configuration, such as a configuration exhibiting one or more of different dimensions, a different shape, different features, different feature spacing, different components, and a different arrangement of components. FIG. 3 illustrates just one non-limiting example of the detector assembly 108. The detector assembly 108 may, for example, include a different configuration of one or more of the gamma ray well detector 122 (including the well 124 therein) and the light sensor 126, and/or a different arrangement of the gamma ray well detector 122 and the light sensor 126.

Figure 4:
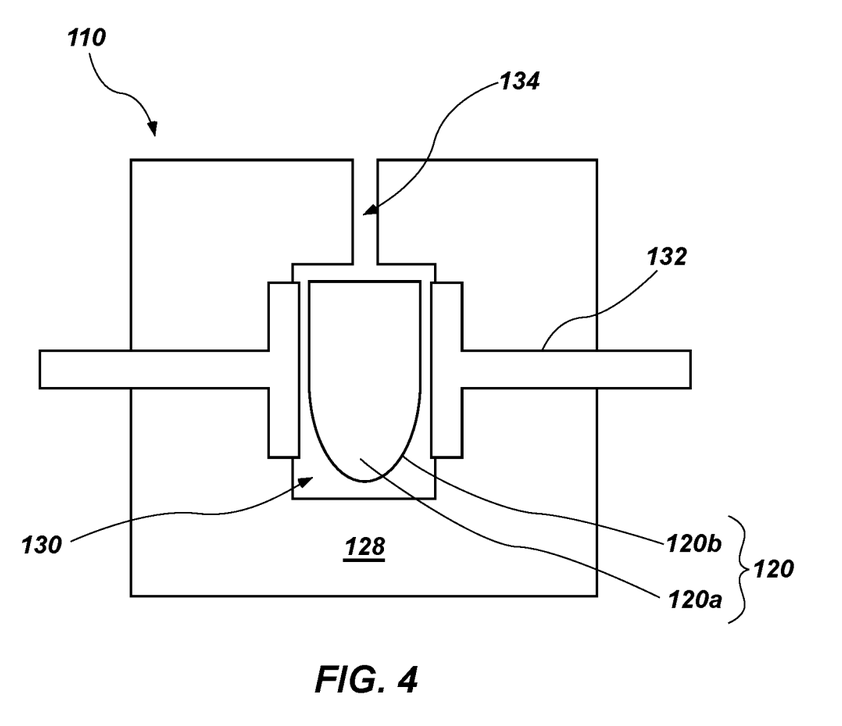
FIG. 4 is a simplified, cross-sectional view of a scintillation cell destruction assembly of the radioactive gas assay system shown in FIG. 1, in accordance with an embodiment of the disclosure.

FIG. 4 is a simplified, cross-sectional view of the scintillation cell destruction assembly 110, in accordance with an embodiment of the disclosure. As shown in FIG. 4, the scintillation cell destruction assembly 110 may include a containment vessel 128 at least partially defining an internal chamber 130 and a radioactive gas outlet 134 in fluid communication with the internal chamber 130, and a rupturing device 132 operatively associated with the containment vessel 128. As described in further detail below, the scintillation cell destruction assembly 110 may be configured to receive the scintillation cell 120 from the detector assembly 108 (FIG. 3), to rupture (e.g., crush, crack, break) the glass scintillator shell 120b of the scintillation cell 120 to release (e.g., discharge, liberate) the volume of radioactive gas 120a of the scintillation cell 120, and to direct the newly-released volume of radioactive gas 120a out of the scintillation cell destruction assembly 110.

The containment vessel 128 of the scintillation cell destruction assembly 110 is configured and operated to receive and hold the scintillation cell 120 within the internal chamber 130 thereof, and to direct the volume of radioactive gas 120a released from the scintillation cell 120 upon subsequent rupture of the glass scintillator shell 120b (e.g., using the rupturing device 132) through the radioactive gas outlet 134. The containment vessel 128 (including the internal chamber 130 and the radioactive gas outlet 134 thereof) may exhibit any dimensions, shape, features, feature spacing, components, and arrangement of components compatible with the configuration (e.g., dimensions, shape, material composition, etc.) of a scintillation cell 120.

With continued reference to FIG. 4, the rupturing device 132 of the scintillation cell destruction assembly 110 is configured and operated to apply sufficient force (e.g., compressive force) to the scintillation cell 120 to rupture the glass scintillator shell 120b thereof. The rupture of the glass scintillator shell 120b may terminate the containment of the volume of radioactive gas 120a and permit the volume of radioactive gas 120a to be retrieved (e.g., by way of negative pressure applied through a vacuum manifold) and utilized again, as desired. By way of non-limiting example, the rupturing device 132 may comprise a crushing device (e.g., a mechanical crusher, a hydraulic crusher, a pneumatic crusher) configured and operated to apply force to one or more sides of the glass scintillator shell 120b of the scintillation cell 120.

The volume of radioactive gas 120a exiting the scintillation cell destruction assembly 110 may be utilized as desired. Referring again to FIG. 1, in some embodiments, at least a portion of the volume of radioactive gas 120a (FIG. 4) exiting the scintillation cell destruction assembly 110 may be directed (e.g., recycled) back into one or more of the radioactive gas source 104 and the scintillation cell production assembly 106. Recycling at least a portion of the volume of radioactive gas 120a may enhance the efficiency and versatility of the radioactive gas assay system 100, while minimizing radioactive waste and the costs and risks that may otherwise be associated with the transport and disposal of radioactive waste.

The systems, methods, devices, and structures of the disclosure advantageously facilitate the assay of a volume of radioactive gas (e.g., for radiation detector calibration through conventional methodologies, such as absolute efficiency calibration methodologies) without the destruction (e.g., at least partial loss) of the volume of radioactive gas. A scintillation cell produced and analyzed according to embodiments of the disclosure may completely retain a volume of radioactive gas until it is desired to retrieve the volume of radioactive gas. When such retrieval is desired, the volume of radioactive gas may be non-destructively (e.g., completely) recovered from the scintillation cell, and subsequently used again as desired. In addition, scintillation cells according embodiments of the disclosure may be formed to contain different types and amounts of radioactive isotopes (e.g., radioxenon isotopes), to accommodate the needs (e.g., calibration needs) of various radiation detection devices and systems. The systems, methods, devices, and structures of the disclosure may be more efficient (e.g., material efficient, time efficient, cost efficient), more accurate, and more adaptable and as compared to conventional systems, conventional methods, conventional devices, and conventional structures for assaying a radioactive gas.

While the disclosure is susceptible to various modifications and alternative forms, specific embodiments have been shown by way of example in the drawings and have been described in detail herein. However, the disclosure is not limited to the particular forms disclosed. Rather, the disclosure is to cover all modifications, equivalents, and alternatives falling within the scope of the following appended claims and their legal equivalent.

What is claimed is:
1. A radioactive gas assay system, comprising:
 a scintillation cell production assembly configured to produce a scintillation cell comprising a glass scintillator shell containing a volume of radioactive gas;
 a detector assembly configured to receive the scintillation cell and to detect photons emitted by the scintillation cell;
 a computer assembly operatively associated with and configured to receive data from the detector assembly to automatically calculate an absolute activity of the volume of radioactive gas of the scintillation cell as well as radiation detection efficiencies of the detector assembly; and a scintillation cell destruction assembly configured to receive the scintillation cell and to rupture the glass scintillator shell thereof to release the volume of radioactive gas contained therein.

2. The radioactive gas assay system of claim 1, wherein the scintillation cell production assembly comprises:

a retention device configured to receive and hold a preliminary glass scintillator structure;

a gas delivery device configured to connect to the preliminary glass scintillator structure and to deliver radioactive gas into a cavity in the preliminary glass scintillator structure to form a gas-filled preliminary glass scintillator structure; and a sealing device configured and positioned to seal and separate a portion of the gas-filled preliminary glass scintillator structure to form the scintillation cell.

3. The radioactive gas assay system of claim 1, wherein the scintillation cell production assembly is configured to form the glass scintillator shell of the scintillation cell from a glass scintillator material formulated to completely contain the volume of radioactive gas and to substantially prevent transmission of beta radiation therethrough while substantially permitting photon emission from the scintillation cell.

4. The radioactive gas assay system of claim 1, wherein the detector assembly comprises:

a gamma ray well detector configured to receive and removably hold the scintillation cell in an opening therein and to detect gamma photons emitted from the scintillation cell; and a light sensor configured to at least partially extend into the opening in the gamma ray well detector and to detect scintillation photons emitted from the scintillation cell.

5. The radioactive gas assay system of claim 4, wherein the gamma ray well detector comprises a high-purity germanium well detector, and wherein the light sensor comprises a photomultiplier tube.

6. The radioactive gas assay system of claim 4, wherein the computer assembly is configured to receive gamma photon counts from the gamma ray well detector and scintillation photon counts from the light sensor, and to automatically calculate the absolute activity of the volume of radioactive gas of the scintillation cell, a beta detection efficiency of the detector assembly, and a gamma detection efficiency of the detector assembly at least partially based on the received gamma photon counts and the received scintillation photon counts.

7. The radioactive gas assay system of claim 1, wherein the scintillation cell destruction assembly comprises:

a containment vessel configured to receive and hold the scintillation cell; and a device configured and positioned to rupture the glass scintillator shell of the scintillation cell to release the volume of radioactive gas contained therein.

8. The radioactive gas assay system of claim 1, further comprising a radiative gas source in fluid communication with the scintillation cell production assembly, the radiative gas source configured to hold a radioactive gas comprising one or more of $^{127}$Xe, $^{131m}$Xe, $^{133}$Xe, $^{133m}$Xe, $^{135}$Xe and to direct the radioactive gas to the scintillation cell production assembly.

9. The radioactive gas assay system of claim 8, further comprising a manifold configured and positioned to direct the volume of radioactive gas released from the scintillation cell by the scintillation cell destruction assembly into one or more of the radiative gas source and the scintillation cell production assembly.

10. A method of assaying a radioactive gas, comprising:

forming a scintillation cell comprising a substantially non-porous glass scintillator shell containing a volume of radioactive gas;

delivering the scintillation cell into a detector assembly comprising a gamma well detector and a light sensor to detect photons emitted from the scintillation cell;

calculating an absolute activity of the volume of radioactive gas of the scintillation cell and radiation detection efficiencies of the detector assembly using a computer assembly in communication with the detector assembly; and removing the scintillation cell from the detector assembly.

11. The method of claim 10, wherein forming a scintillation cell comprises:

delivering a radioactive gas comprising one or more radioxenon isotopes into a preliminary glass scintillator structure comprising a substantially non-porous glass scintillator material to form a gas-filled preliminary glass scintillator structure; and sealing and separating a portion of the gas-filled preliminary glass scintillator structure.

12. The method of claim 11, further comprising:

selecting the radioactive gas to comprise one or more of $^{127}$Xe, $^{131m}$Xe, $^{133}$Xe, $^{133m}$Xe, $^{135}$Xe and selecting the substantially non-porous glass scintillator material to comprise a cerium activated lithium silicate glass scintillator having a density within a range of from about 2.40 g/cm$^3$ to about 2.65 g/cm$^3$.

13. The method of claim 10, wherein delivering the scintillation cell into a detector assembly comprises:

delivering the scintillation cell into an opening in the gamma well detector, the scintillation cell remaining substantially unattached to surfaces of the gamma well detector within the opening; and inserting the light sensor into the opening in the gamma well detector to overlie the scintillation cell within the opening.

14. The method of claim 10, wherein delivering the scintillation cell into a detector assembly comprising a gamma well detector and a light sensor to detect photons emitted from the scintillation cell comprises:

selecting the gamma well detector to comprise a high-purity germanium well detector;

selecting the light sensor to comprise a photomultiplier tube;

detecting and counting gamma photons emitted from the scintillation cell using the high-purity germanium well detector; and detecting and counting scintillation photons emitted from the scintillation cell using the photomultiplier tube.

15. The method of claim 14, wherein calculating an absolute activity of the volume of radioactive gas of the scintillation cell and radiation detection efficiencies of the detector assembly comprises automatically calculating the absolute activity of the volume of radioactive gas of the scintillation cell, a beta detection efficiency of the detector assembly, and a gamma detection efficiency of the detector assembly using the computer assembly at least partially based on gamma photon counts and scintillation photon counts received from the high-purity germanium well detector and the photomultiplier tube.

16. The method of claim 10, further comprising:
rupturing the substantially non-porous glass scintillator shell of the scintillation cell after removing the scintillation cell from the detector assembly to release the volume of radioactive gas contained within the substantially non-porous glass scintillator shell; and
recovering at least a portion of the volume of radioactive gas released upon rupturing the substantially non-porous glass scintillator shell.

17. The method of claim 16, wherein rupturing the substantially non-porous glass scintillator shell of the scintillation cell comprises applying force to the substantially non-porous glass scintillator shell.

\* \* \* \* \*